United States Patent [19]

Uemura et al.

[11] 4,343,736

[45] Aug. 10, 1982

[54] PROCESS FOR RECOVERING INTERFERON

[75] Inventors: Yahiro Uemura, Hirakata; Hirofumi Arimura, Toyonaka; Hiroshi Morise, Hirakata; Satoshi Funakoshi, Katano; Tadakazu Suyama, Kyoto, all of Japan

[73] Assignee: The Green Cross Corporation, Osaka, Japan

[21] Appl. No.: 280,687

[22] Filed: Jul. 6, 1981

Related U.S. Application Data

[62] Division of Ser. No. 175,744, Aug. 6, 1980, Pat. No. 4,314,935.

[30] Foreign Application Priority Data

Oct. 5, 1979 [JP] Japan .................................. 54-128513

[51] Int. Cl.$^3$ ........................ A61K 45/02; C07G 7/00
[52] U.S. Cl. .................................. 260/112 R; 424/85; 435/68; 435/811; 536/21
[58] Field of Search ...................... 260/112 R; 424/85; 435/811, 68; 536/21

[56] References Cited

U.S. PATENT DOCUMENTS 3,144,390 8/1964 Burke ..................................... 424/85
4,172,071 10/1979 De Maeyer et al. ................. 424/85

*Primary Examiner*—Blondel Hazel
*Attorney, Agent, or Firm*—Cushman, Darby & Cushman

[57] ABSTRACT

A process for recovering interferon which comprises contacting a solution containing an interferon produced by the induced cells of human origin with a water-insolubilized sulfated polysaccharide to allow the interferon to be adsorbed on the water-insolubilized sulfated polysaccharide and then selectively eluting the interferon with an aqueous solution of an inorganic salt.

7 Claims, No Drawings

PROCESS FOR RECOVERING INTERFERON

This is a division, of application Ser. No. 175,744 filed Aug. 6, 1980 now U.S. Pat. No. 4,314,935.

This invention relates to a process for recovering on an industrial scale an interferon produced by induced cells of human origin.

Interferon is a certain type of glycoprotein induced in human and other animal cells by viral or other stimuli. The interferon has an inhibitory action for the growth of virus, bacteria, or protozoa in cells. In order to apply it in man as a medicine, it is necessary to obtain the interferon produced in human cells because of its species specificity. To obtain large quantities of human interferon, it is necessary to collect a large quantity of human lymphocytes, human fibroblasts, or human lymphoblasts of the established line, then to stimulate them by suitable means to produce the interferon, and to recover the formed interferon in a high yield. The conventional recovering methods, however, are too complicated in the procedure and are too time-consuming to be carried out on a commercial scale, and they have an additional disadvantage of low material yield.

The present inventors had conducted researches for many years on the method of recovering interferon easily and in high yield. As a result, it was found for the first time that a sulfated polysaccharide such as heparin, chondroitin sulfate, dextran sulfate or the like is capable of binding the interferon in a specific manner. On continuation of the research of the purpose of recovering interferon on an industrial scale by taking the above phenomenon to advantage, it has been found that a large quantity of interferon can be recovered in a short period of time by allowing a sulfated polysaccharide to be water-insoluble by combining with a carrier capable of insolubilizing the sulfated polysaccharide by known ways, adsorbing and combining interferon on said water-insolubilized sulfated polysaccharide and then eluting the interferon therefrom.

An object of this invention is to provide a novel method for recovering an interferon produced by the induced cells of human origin.

Other objects and advantages of this invention will become apparent from the following description.

According to this invention, there is provided a process for recovering interferon, which comprises contacting a solution containing an interferon produced by the induced cells of human origin with a water-insolubilized sulfated polysaccharide to allow the interferon to be adsorbed on the water-insolubilized sulfated polysaccharide and then selectively eluting the interferon with an aqueous solution of an inorganic salt.

The above-mentioned method may also be effected in such a way that interferon is allowed to be adsorbed on a sulfated polysaccharide, the interferon adsorbed sulfated polysaccharide is brought into contact with a carrier such as an ion exchange resin capable of water-insolubilizing the sulfated polysaccharide to render the sulfated polysaccharide insoluble in water, and then the interferon is eluted with an aqueous solution of an inorganic salt.

The method of this invention is described below in further detail.

To render a sulfated polysaccharide insoluble in water, it is convenient to follow the method of P. Cuatrecasas [J.B.C., 245, (12), 3059 (1970)] for attaching a sulfated polysaccharide to a carrier. It is carried out by activating a water-insoluble high molecular weight polysaccharide as carrier such as, for example, Sepharose, agarose or cellulose with cyanogen bromide or water-soluble carbodiimide, and allowing the activated material to react with a polysaccharide sulfate. Other methods may also be used. For instance, ion-exchange resins having amino or carboxyl group such as diethylaminocellulose, carboxymethylcellulose, or Amberlite IRC-50 (trademark for polyacrylic acid having carboxyl groups, manufactured by Rohm & Hass Co.) may also be used as the water-insoluble carrier. These resins readily attach to a sulfated polysaccharide in the presence of water-soluble carbodiimide.

The sulfated polysaccharides which can be used are heparin, chondroitin sulfate, dextran sulfate, cellulose sulfate, and sodium or potassium salt thereof. In the process of this invention, an aqueous solution containing interferon is brought into contact with a water-insoluble carrier bearing a chemically combined polysaccharide sulfate or an alkali metal salt thereof.

The starting material for use in the process of this invention can be a human cell culture containing induced interferon or a material partially purified therefrom by the ammonium sulfate fractionation, ion-exchange adsorption, or bentonite adsorption.

The sulfated polysaccharide used in this invention is known to adsorb antithrombin-III or other blood coagulation factors. If there is any fear of contamination with such substances, these must be removed prior to use or during the course of processing. An effective means for this purpose is the bentonite adsorption or gel filtration. By combining the process of this invention with these purification treatments, it is feasible to yield highly pure interferon on a large scale.

Examples of other purification methods suitable for use in combination with the present process include ethanol fractionation (Tissue Culture Association, In Proceedings of a Tissue Culture Association Work Shop in Vitro, Report No. 3, 1973); a method in which column chromatography and gel filtration are combined by using weakly acidic and weakly basic ion-exchangers (Japanese Patent Publication No. 34,442/76); a method employing ammonium chloride or dextran [Ann. Med. Exp. Bio. Fenn., 44, 265–273 (1966); Ditto, 45, 20–29 (1967)]; and fractionation by the use of a strongly acidic cation exchanger (Japanese Patent Application Kokai (Laid-Open) No. 89011/79).

The cells of human origin for use in the present process are leukocytes, lymphocytes, reticuloendothelial cells such as cells of peritoneal cavity, lung and spleen, cultured human lymphoblast-like cells, and other known cells capable of producing interferon. Preferred in view of productivity are human leukocytes and cultured human lymphoblast-like cells, particularly Namalva strain. The Namalva strain is an established cell line selected from 20 established lymphocyte cell lines originated from Burkitt's lymphoma and leukemia patients. It is known as a cell most productive of interferon [Intern. J. Cancer, 11, 327 (1973)].

Although the water-insolubilized sulfated polysaccharide for use in separating interferon is only needed to be washed with water before use, it is preferably kept equilibrated with a buffer solution of pH 5 to 10. The buffer solution is preferably adjusted to a salt concentration of 0.5 moles/liter or less, most preferably 0.3 moles/liter or less. The aqueous solution containing interferon is also adjusted preferably to the same salt concentration and the same pH as above-noted. The adsorption of interferon from the aqueous solution is effected, for example, by contacting the aqueous solution containing crude interferon with a sulfated polysaccharide borne by the insoluble carrier preferably packed in a column.

The interferon adsorbed on the water-insoluble sulfated polysaccharide is eluted from the carrier with an aqueous solution of a salt concentration of 0.5 to 2 moles/liter. The salt used in the aqueous solution can be an inorganic salt of an alkali metal or alkaline earth metal such as sodium chloride, potassium chloride, calcium chloride or sodium sulfate. Of these salts, sodium chloride most preferably used. The hydrogen ion concentration of the aqueous solution for use in the adsorption and elution treatments is in the range of from pH 5 to pH 10.

The recovery of interferon according to this invention is higher than that of conventional processes and amounts to more than 70% and the necessary steps of treatment are only the contact by an aqueous interferon solution with an insolubilized polysaccharide sulfate and the elution of interferon with an aqueous inorganic salt solution. Since these steps of treatment are both simple and easy to perform, the present process is suitable for the commercial production of interferon.

The invention is illustrated below with reference to Examples, but the invention is not limited thereto. In Examples, the potency of interferon was determined by the method of 50% plaque reducton using vesicular stomatitis virus and the FL cell originated from human amnion. The titer of interferon was expressed in international unit (IU) calculated from the assay of the sample under test and the standard sample of interferon ["Saishin Iyaku" (Modern Medicine), 29, (4) 660 (1974)].

EXAMPLE 1

Lymphocytes originated from the human vein were cultivated in MEM medium containing 0.25% of human albumin and interferon was induced by Sendai virus. The culture liquor was adjusted to pH 2 with hydrochloric acid to inactivate the Sendai virus used as inducer. The rsulting raw interferon liquor was centrifuged to collect the supernatant. To 1 liter of the supernatant, was added 2.0 g of bentonite to adsorb the interferon. The bentonite was collected by centrifugation and suspended in a 1% ammonium sulfate solution followed by centrifugation. This treatment was repeated three times while washing the bentonite each time to remove impurities. The washed bentonite was admixed with a 0.5% acrinol solution (pH 2.5) and stirred at 37° C. for 30 minutes to elute the interferon. The eluate was adjusted to pH 7 with 4 N sodium hydroxide solution and admixed with a small amount (5 g) of CM-Sephadex (Pharmacia Co.) to remove acrinol by adsorpton.

A heparin-sepharose column was prepared by attaching heparin to Sepharose 4 B which had been activated with cyanogen bromide according to the method of P. Cuatrecasas and packing the heparin-sepharose in a 50-ml column. The column was equilibrated with 0.9% sodium chloride solution. The crude eluate obtained above was fed to the heparin-sepharose column to adsorb the interferon. The column was washed with a 0.9% sodium chloride solution to remove impurities until the O.D. (Opitical Density) 280 nm had become 0.050 or less. The concentration of sodium chloride was then raised to 2 M to elute the interferon. The fractions by high interferon activities [Saishin Iyaku (Modern Medicine), 29, (4) 660 (1974)] were pooled, concentrated by ultrafiltration, and dialyzed by cellophane tube against a physiological saline to obtain purified interferon.

The overall recovery of the interferon activity was 48%, assuming the activity of starting material to be 100% and the recovery was 80%, assuming the activity before adsorption on the column to be 100%. The purification was 5,100-fold based on the starting material.

A concentrated solution of the purified interferon was passed through a sterile bacterial filter. The filtrate was subdivided into portions and each lyophilized to obtain a dry preparation. Mice and rabbits were administered with the above preparation at a dosage of 1,000,000 IU/kg and were observed for 7 days. No extraordinary increase or decrease in body weight and pilocrection was detected.

EXAMPLE 2

Human lymphoblasts of an established cell line were induced by Sendai virus to produce interferon. After inactivation of the Sendai virus, there was obtained a culture liquor containing interferon. To 20 liters of the culture liquor, was added 2 kg on wet basis of SP-Sephadex to adsorb thereon the interferon. The contaminant proteins were removed by washing with a 0.01 M acetate buffer (pH 4) containing 0.4% of sodium chloride. The adsorbed interferon was eluted with a 0.10 M phosphate buffer (ph 8.0). The heparin-sepharose obtained in Example 1 was packed in a 1,000-ml column. The column was equilibrated with 0.01 M acetate buffer solution (ph 5.0). To this column, was fed the above eluate from the SP-Sephadex to adsorb the interferon on the column. After removal of the contaminant proteins as in Example 1, the interferon was eluted with a 2 M sodium chloride solution containing 0.02% of chondroitin sulfate (average molecular weight, 4,000) to obtain a purified interferon solution.

The overall recovery of interferon activity was 80% based on the starting material, the purification having been 4,200-fold. The dried preparation of the recovered interferon was administered to mice and rabbits, without noticing any abnormality.

What is claimed is:

1. A process for recovering interferon, which comprises contacting a solution containing interferon produced by the induced cells of human origin with a water-insolubilized heparin to allow the interferon to be adsorbed on the water-insolubilized heparin and then eluting the interferon with an aqueous solution containing an inorganic salt and chondroithin sulfate.

2. A process according to claim 1, wherein the inorganic salt is sodium chloride, potassium chloride, calcium chloride or sodium sulfate.

3. A process according to claim 1, wherein the cells of human origin is leukocytes, lymphocytes or reticuloendothelial cells.

4. A process according to claim 3, wherein the cells of human origin is Namalva strain.

5. A process according to claim 1, wherein the water-insolubilized heparin is washed with water before use.

6. A process according to claim 5, wherein the water-insolubilized heparin is kept equilibrated with a buffer solution of pH 5 to 10.

7. A process according to claim 1, wherein the salt concentration and pH of the aqueous solution is 0.05 to 2 moles/liter and 5 to 10, respectively.

* * * * *